United States Patent [19]

Schmidhauser et al.

[11] Patent Number: 5,312,918

[45] Date of Patent: May 17, 1994

[54] METHOD FOR PREPARING SUBSTITUTED NITROGEN-HETEROCYCLIC COMPOUNDS

[75] Inventors: John C. Schmidhauser, Schenectady; Kathryn L. Longley, Saratoga Springs; William L. Gately, Burnt Hills, all of N.Y.

[73] Assignee: General Electric Company, Schenectady, N.Y.

[21] Appl. No.: 65,381

[22] Filed: May 24, 1993

Related U.S. Application Data

[63] Continuation-in-part of Ser. No. 795,577, Oct. 21, 1991, abandoned, which is a continuation-in-part of Ser. No. 620,678, Dec. 3, 1990, abandoned.

[51] Int. Cl.$^5$ ............................................. C07D 251/30
[52] U.S. Cl. ..................................... 544/218; 544/219
[58] Field of Search .............................. 544/218, 219

[56] References Cited

U.S. PATENT DOCUMENTS 4,895,945 1/1990 Brown et al. ...................... 544/218

OTHER PUBLICATIONS

Heterocyclic Chemistry, Albert, pp 50-53, 116, The Athlone Press, 1968.
Synthesis, Alsaidi et al, pp. 921-924, 1980.

*Primary Examiner*—Mukund J. Shah
*Assistant Examiner*—Y. N. Gupta
*Attorney, Agent, or Firm*—William H. Pittman

[57] ABSTRACT

Halo-displacement reaction products of aliphatic hydroxy compounds and chloro- or bromo-substituted aromatic nitrogen-heterocyclic compounds are conducted under alkaline conditions in the presence of a phase transfer catalyst, in the substantial absence of water inorganic salts other than those formed in the reaction. The method is particularly useful for the preparation of substituted chlorotriazines. In a preferred embodiment, the reagents constitute at least about 25% by weight of the organic phase of the reaction mixture.

18 Claims, No Drawings

METHOD FOR PREPARING SUBSTITUTED NITROGEN-HETEROCYCLIC COMPOUNDS

This application is a continuation-in-part of copending application Ser. No. 07/795,577 filed Oct. 21, 1991, now abandoned, which in turn is a continuation-in-part of Ser. No. 07/620,678, filed Dec. 03, 1990, now abandoned.

This invention relates to the preparation of substituted triazines and similar substituted heterocyclic compounds.

Various methods are known for conducting reactions between chloro- or bromo-substituted aromatic nitrogen-heterocyclic compounds and aliphatic alcohols. Reactions of this type are exemplified by the reactions of halo-substituted 1,3,5-triazines with unsubstituted or substituted alkanols, including epoxy-, phosphate- and ortho ester-substituted alkanols. The products, which are chlorotriazines containing radicals derived from the unsubstituted or substituted alkanol, are useful, for example, as reagents for reactive capping of polyphenylene ethers and similar polymers.

U.S. Pat. No. 4,895,945, for example, describes the reaction of cyanuric chloride and alkyl or aryl chlorocyanurates with glycidol to form mono- and diglycidoxy-substituted triazines. Said reaction is conducted in an organic solvent such as methylene chloride, by gradual addition of the glycidol and of aqueous base to a solution of a chloro-substituted triazine.

In the examples of said patent, an excess of glycidol in the amount of 200% of stoichiometric or greater are employed. Such high proportions of glycidol are undesirable by reason of its relatively high cost and its hazardous tendencies. Other areas in which there is room for improvement include maximization of product yield and simplification of the reaction procedure.

The present invention is based on the discovery of various modifications in the above-described reaction process which contribute materially to improvement of yield and to the ability to conduct the reaction in a minimum of time and under relatively simple conditions, using a reduced amount of glycidol or similar aliphatic hydroxy compound. Included are both mandatory and optional modifications. The method has wide applicability to a number of halo-substituted aromatic nitrogen-heterocyclic compounds and a number of unsubstituted and substituted aliphatic alcohols.

Accordingly, the invention is a method for preparing a halo-displacement reaction product of (A) an aliphatic hydroxy compound and (B) an aromatic heterocyclic compound containing (1) at least two nuclear nitrogen atoms or (2) at least one nuclear nitrogen atom and at least one electron-withdrawing group, said atom or group activating a chloro- or bromo-substituted carbon atom adjacent to said nitrogen atom, which comprises effecting contact between reagents A and B in solution in a substantially water-immiscible organic solvent under alkaline conditions, in the presence of a phase transfer catalyst and in the substantial absence of inorganic salts other than those formed in the reaction.

Reagent A employed in the method of this invention is an aliphatic hydroxy compound. Any such compound may be employed; included are both unsubstituted and substituted alkanols. Reagent A may be a simple alkanol such as methanol, ethanol, 1-propanol, 2-propanol, 1-butanol, 1-hexanol or 2-ethylhexanol; an epoxy-substituted alkanol such as glycidol (2,3-epoxy-1-propanol); a halo- or phosphate-substituted alkanol such as 2-chloro-1-ethanol, dimethyl 2-hydroxyethyl phosphate or di-n-butyl 2-hydroxyethyl phosphate; or a cyclic ortho ester such as 4-hydroxymethyl-2-methoxy-2-methyl-1,3-dioxolane and 4-hydroxy-1-methyl-2,6,7-trioxabicyclo[2.2.2]octane. The invention has been found particularly useful with the epoxy-, dialkyl phosphate- and cyclic ortho ester-substituted alkanols, and especially the epoxy-substituted alkanols.

Reagent B is an aromatic nitrogen-heterocyclic compound with certain molecular features including a chloro or bromo substituent on a carbon atom adjacent to a nitrogen atom and one of the following: (1) at least two nuclear nitrogen atoms or (2) at least one such atom in combination with at least one electron-withdrawing group activating said chloro or bromo substituent. Suitable electron-withdrawing groups are nitro, carbalkoxy, perfluoroalkyl and acyl substituents and other nitrogen hetero atoms.

The heterocyclic compound usually contains a 6-membered ring. A wide variety of such compounds may be employed including those having the following heterocyclic nuclei, all substituents except the chloro or bromo substituents being omitted in these formulas:

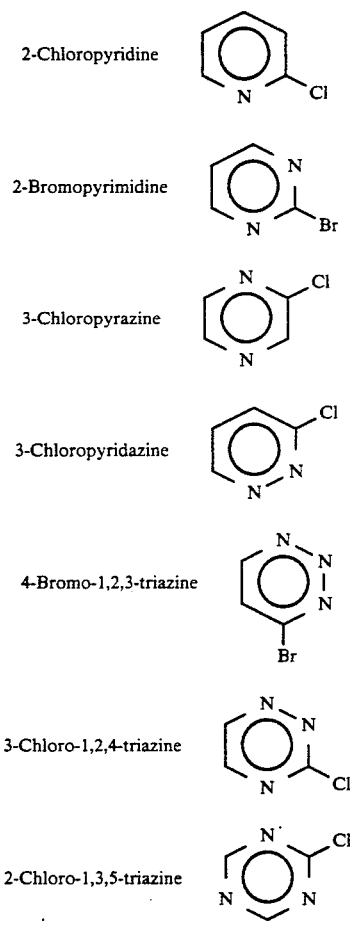

2-Chloropyridine

2-Bromopyrimidine

3-Chloropyrazine

3-Chloropyridazine

4-Bromo-1,2,3-triazine

3-Chloro-1,2,4-triazine

2-Chloro-1,3,5-triazine

The preferred heterocyclic compounds are those containing at least 2 and preferably 3 nuclear (i.e., heterocyclic) nitrogen atoms, whereupon the second such nitrogen atom serves as the activating group for the chloro or bromo substituent. 1,3,5-Triazines are especially preferred, with the alkoxy- or aryloxy-substituted chloro-1,3,5-triazines being most preferred; examples are 2,4-dichloro-4-n-butoxy-1,3,5-triazine and 2,4-dichloro-4-(2,4,6-trimethylphenoxy)-1,3,5-triazine.

According to the present invention, the halo-displacement reaction between reagents A and B is conducted in a substantially water-immiscible organic solvent. Suitable solvents include aromatic hydrocarbons such as toluene and xylene, chlorinated aromatic hydrocarbons such as chlorobenzene and o-dichlorobenzene, and chlorinated aliphatic hydrocarbons such as methylene chloride and chloroform. Methylene chloride and toluene are particularly suitable, with toluene frequently being preferred by reason of its relative environmental harmlessness.

The invention requires the employment of a phase transfer catalyst. Any such catalyst known in the art may be employed; examples of suitable types of compounds are quaternary ammonium and phosphonium salts, hexaalkylguanidinium salts and crown ethers. Quaternary ammonium salts are frequently preferred because of their effectiveness and relative availability. Particularly preferred are methyltrialkylammonium salts wherein the alkyl groups contain about 8-20 carbon atoms, as illustrated by "Adogen 464" in which the alkyl groups contain 8-10 carbon atoms.

Another essential feature is the substantial absence of inorganic salts, other than those formed in the reaction between reagents A and B. Other inorganic salts, such as those which may have been formed in the course of a previous reaction to prepare reagent B, should be removed by filtration, decantation of liquid or the like prior to the reaction.

For example, it is frequently convenient to effect reaction between cyanuric chloride and a compound such as n-butanol or 2,4,6-trimethylphenol (mesitol) to prepare a monoalkyl or monoaryl dichlorocyanurate, which then undergoes further reaction with glycidol to form 2-chloro-4-butoxy-6-glycidoxy-1,3,5-triazine or 2-chloro-4-mesitoxy-6-glycidoxy-1,3,5-triazine. In the course of the first reaction, sodium chloride is formed and water is added, usually in the form of aqueous base. It has been found that the time required for the second reaction is relatively long when said sodium chloride and water are not removed from the reaction mixture prior to further reaction with glycidol. If salt and water removal takes place according to this invention, the reaction time can be decreased significantly, typically to 1/6 of the time required if separation does not take place. It is not necessary in this example, however, to continuously remove salts during the reaction of the intermediate with glycidol.

The method of this invention is conducted under alkaline conditions, most often in the presence of an aqueous metal hydroxide such as sodium hydroxide or potassium hydroxide. Fairly concentrated aqueous base solutions, most often at least about 40% by weight, are usually employed. The proportion of base is usually about 10-25% in excess of the stoichiometric amount. Most often, the base is added gradually or incrementally to the other reagents.

Reaction temperatures according to the invention may be in the range of about 0°-70° C. Temperatures of about 10°-25° C. are generally preferred since they result in the formation of a minimum of by-products.

One benefit of the method of this invention is a substantial decrease in the amount of reagent A required. As previously noted, U.S. Pat. No. 4,895,945 discloses the employment of glycidol in 200% excess or greater. In the present invention, on the other hand, it is necessary to employ reagent A in amounts only up to about 30% in excess of stoichiometric. The desired reaction product is nevertheless obtained in high yield, frequently above 80% of theoretical.

In a preferred embodiment of the invention, reagents A and B are present in the amount of at least about 25% by weight of the organic phase. That is, reagents A and B together constitute at least about 25% of the total weight of reagent A, reagent B and organic solvent. At such concentrations, the reaction rate is increased and the amount of time necessary for completion of the reaction is further diminished. The especially preferred proportion of reagents A and B is from about 25% to the amount affording a saturated solution.

Following completion of the reaction, it is possible to recover product by conventional means including stripping of the organic solvent. It is frequently desirable, however, to employ substituted chlorotriazines as capping agents for polyphenylene ethers in the form of a solution in an organic solvent, typically an aromatic hydrocarbon such as toluene. When a chlorinated aliphatic hydrocarbon such as methylene chloride is employed in the method of this invention, it may be replaced by a higher boiling solvent (e.g., toluene) by a combination of addition of the desired solvent and vacuum stripping or distillation at atmospheric or reduced pressure, the stripping and/or distillation steps taking place in one or two stages. For example, methylene chloride may be replaced by toluene by first removing a major proportion of the methylene chloride by distillation at atmospheric pressure, followed by addition of toluene and vacuum stripping of the remaining methylene chloride.

The invention is illustrated by the following examples.

EXAMPLE 1

A 100-gallon reactor fitted with an agitator, thermocouple probe, reflux condenser, addition funnel and nitrogen charge means was charged with 147 kg. of methylene chloride and 24.4 kg. (179.4 moles) of mesitol as a melt at 80° C. The reactor was cooled to 5° C. and there were added 31.5 kg. (170.8 moles) of cyanuric chloride and 920 grams of "Adogen 464". The reactor was further cooled to 2° C. and 15 kg. (187.9 moles) of 50% aqueous sodium hydroxide solution was added slowly, with further cooling to maintain the temperature below 15° C. The mixture was stirred under nitrogen for 1 hour following the completion of sodium hydroxide addition.

The precipitated salts were allowed to settle and the organic solution was separated. The salts were treated with 38 liters of deionized water and 11.4 liters of methylene chloride. The methylene chloride layer was combined with the reaction mixture in the cleaned reactor.

The mixture was again cooled to 5° C. and 15.8 kg. (213.5 moles) of glycidol was added, followed by slow addition of an additional 16.4 kg. (205 moles) of sodium hydroxide solution. The temperature was maintained below 25° C. during sodium hydroxide addition, and then at 25° C. for an additional hour.

The organic solution was washed four times with deionized water and distilled at atmospheric pressure to remove 144 kg. of methylene chloride. Toluene, 160 kg., was added and the remaining methylene chloride was removed by vacuum distillation at 50 torr. There was obtained 151 kg. of a 1.04M solution in toluene of the desired 2-chloro-4-mesitoxy-6-glycidoxy-1,3,5-triazine (82% of theoretical).

EXAMPLE 2

The reactor of Example 1 was charged with 96 kg. of toluene, and 14 kg. (102.9 moles) of mesitol was added as a melt. The solution was cooled to 5° C. and there were added 18 kg. (97.6 moles) of cyanuric chloride and 500 grams of "Adogen 464". There was then added under nitrogen, with stirring, 8.6 kg. (107.4 moles) of 50% aqueous sodium hydroxide solution over 2 hours, as the mixture was maintained at 5°-15° C. The mixture was allowed to warm to room temperature and 76 liters of deionized water was added, with stirring, to dissolve inorganic salts.

The aqueous layer was discarded and the organic layer was returned to the reactor at 10° C., whereupon 9 kg. (122 moles) of glycidol was added. It was followed by 9.4 kg. (117.1 moles) of aqueous sodium hydroxide solution, introduced gradually as the reaction mixture was stirred at 15°-20° C. Stirring was continued for 1 hour after base addition was complete.

The mixture was washed with water until it was neutral and the glycidol level was below 50 ppm. It was then distilled under vacuum to remove 18 kg. of a toluene-water azeotrope. The residue was a 0.75M solution in toluene of the desired 2-chloro-4-mesitoxy-6-glycidoxy,3,5-triazine (84% of theoretical).

EXAMPLE 3

A 500-ml. three-necked Morton flask equipped with a mechanical stirrer, addition funnel, nitrogen inlet and thermometer was charged with 40 grams (217 mmol.) of cyanuric chloride, 31 grams (228 mmol.) of mesitol, 150 ml. of methylene chloride and 8 ml. of a 10% wt./vol. solution in toluene of "Adogen 464". (Reagents A and B comprised about 29% by weight of total organic phase.)

The solution was cooled to 0° C. and 19.0 grams (238 mmol.) of 50% aqueous sodium hydroxide solution was added, with stirring, at a rate such that the temperature did not rise above 5° C. After base addition had been completed, the mixture was stirred at 0°-5° C. for 30 minutes, after which high pressure chromatographic analysis showed the reaction to be complete with a product distribution of about 95.6% mesitoxy dichlorocyanurate and 4.4% dimesitoxy chlorocyanurate.

The clear reaction solution was decanted away from the white mass of salt and water which clung to the sides of the reaction flask. The flask was rinsed and cleaned, the solution was reintroduced and 20 grams (270 mmol.) of glycidol was added. Additional sodium hydroxide solution in the amount of 21 grams (262 mmol.) was then introduced at a rate to maintain the temperature at 15°-20° C. The mixture was stirred at room temperature for 1 hour, after which it was shown by analysis to contain the desired 2-chloro-4-mesitoxy-6-glycidoxy-1,3,5-triazine in a total yield of 90.8%. The by-product dimesitoxy chlorocyanurate was present in the amount of 9.2%.

The mixture was washed with water three times, after which it separated cleanly into aqueous and organic layers. The organic layer was removed and toluene was exchanged for the methylene chloride therein as described in Example 1. The total isolated yield of product in the toluene solution was 75-80%.

EXAMPLE 4 (CONTROL)

In a procedure similar to that of Example 3, reagents A and B comprised about 20% of total organic phase and no phase transfer catalyst was employed. In the first step, 250 ml. of methylene chloride, 29.5 grams (217 mmol.) of mesitol and 40 grams (217 mmol.) of cyanuric chloride were employed; in the second step, 21.4 grams (289 mmol.) of glycidol was added. The amounts of sodium hydroxide added in the first and second additions were 17.36 grams (217 mmol.) and 19.1 grams (239 mmol.), respectively. The reaction mixture was not separated from salts and water after the first step. Product yield as shown by analysis after stirring for 3 hours following glycidol addition was only 72.2%; there were also present 9.0% of dimesitoxy chlorocyanurate and 16.8% of mesitoxy dichlorocyanurate as by-products.

Even after stirring at room temperature for 24 hours, product yield by analysis increased to only 86.4%. In addition, 3.4% of unreacted dichlorocyanurate and 10.2% of monochlorocyanuarate were detected. There was a significant layer of emulsion at the interface between the aqueous and organic layers, and separation was difficult. Moreover, each water wash produced an additional quantity of emulsion which resulted in significant product loss. The yield of isolated product was only 60-70%.

These results show the advantage of employing the method of this invention, as compared with the method of the examples of U.S. Pat. No. 4,895,945. Yields are improved even with the use of a decreased proportion of glycidol, and processing is substantially easier when a phase transfer catalyst is employed, water and salts previously formed are removed and reagents A and B comprise at least about 25% of the organic phase. Minor variations in the proportions of mesitol and base are insignificant with respect to the differences in yield and ease of processing.

What is claimed is:

1. A method for preparing a halo-displacement reaction product of (A) an aliphatic hydroxy compound and (B) an alkoxy- or aryloxy-substituted dichloro-1,3,5-triazine, which comprises effecting contact between reagents A and B in solution in a substantially water-immiscible organic solvent under alkaline conditions, in the presence of a phase transfer catalyst and in the substantial absence of inorganic salts other than those formed in the reaction; reagent A being employed in the amount of at most 30% in excess of stoichiometric.

2. A method according to claim 1 wherein the alkaline conditions are maintained by gradual addition of aqueous base.

3. A method according to claim 2 wherein the phase transfer catalyst is a quaternary ammonium and phosphonium salt, hexaalkylguanidinium salt or crown ether.

4. A method according to claim 3 wherein the reaction temperature is in the range of about 10°-25° C.

5. A method according to claim 4 wherein reagent A is employed in the amount of at most about 25% in excess of stoichiometric.

6. A method according to claim 5 wherein the solvent is methylene chloride or toluene.

7. A method according to claim 6 wherein reagent A is an epoxy-, dialkyl phosphate- or cyclic ortho ester-substituted alkanol.

8. A method according to claim 7 wherein reagent A is glycidol, dimethyl 2-hydroxyethyl phosphate, di-n- butyl 2-hydroxyethyl phosphate or 4-hydroxymethyl-2-methoxy-2,3-dioxolane.

9. A method according to claim 8 wherein reagent B is 3,4-dichloro-4-n-butoxy-1,3,5-triazine or 2,4-dichloro-4-(2,4,6-trimethylphenoxy)-1,3,5-triazine.

10. A method according to claim 9 wherein the phase transfer catalyst is a methyltrialkylammonium salt wherein the alkyl groups contain about 8-20 carbon atoms.

11. A method according to claim 4 wherein reagents A and B comprise at least about 25% by weight of the organic phase.

12. A method according to claim 11 wherein reagent A is an epoxy-, dialkyl phosphate- or cyclic ortho ester-substituted alkanol.

13. A method according to claim 12 wherein reagent A is glycidol, dimethyl 2-hydroxyethyl phosphate, di-n-butyl 2-hydroxyethyl phosphate or 4-hydroxymethyl-2-methoxy-2-methyl-1,5-dioxolane.

14. A method according to claim 13 wherein reagent B is 3,4-dichloro-4-n-butoxy-1,3,5-triazine or 2,4-dichloro-4-(2,4,6-trimethylphenoxy)-1,3,5-triazine.

15. A method according to claim 14 wherein the phase transfer catalyst is a methyltrialkylammonium salt wherein the alkyl groups contain about 8-20 carbon atoms.

16. A method according to claim 4 wherein the solvent is toluene.

17. A method according to claim 4 wherein the solvent is methylene chloride.

18. A method according to claim 17 wherein the methylene chloride is replaced by toluene after the reaction is complete.

* * * * *